United States Patent
Sakakibara et al.

(10) Patent No.: US 9,863,943 B2
(45) Date of Patent: Jan. 9, 2018

(54) METHOD OF DETECTING PORK IN PROCESSED FOOD AND DETECTION KIT THEREFOR

(75) Inventors: Yuhiro Sakakibara, Kanagawa (JP); Tatsuya Shuto, Kanagawa (JP); Hisahiko Iwamoto, Kanagawa (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 465 days.

(21) Appl. No.: 13/519,216

(22) PCT Filed: Feb. 18, 2011

(86) PCT No.: PCT/JP2011/053438
§ 371 (c)(1),
(2), (4) Date: Aug. 15, 2012

(87) PCT Pub. No.: WO2011/102437
PCT Pub. Date: Aug. 25, 2011

(65) Prior Publication Data
US 2012/0329073 A1    Dec. 27, 2012

(30) Foreign Application Priority Data
Feb. 18, 2010 (JP) ................................. 2010-034120

(51) Int. Cl.
G01N 33/68    (2006.01)
G01N 33/543   (2006.01)
C07K 16/18    (2006.01)

(52) U.S. Cl.
CPC ....... *G01N 33/54386* (2013.01); *C07K 16/18* (2013.01); *G01N 33/6854* (2013.01)

(58) Field of Classification Search
CPC ......... G01N 33/54386; G01N 33/6854; C07K 16/18
See application file for complete search history.

(56) References Cited

U.S. PATENT DOCUMENTS

| | | | |
|---|---|---|---|
| 5,910,446 A * | 6/1999 | Ansfield | G01N 33/68 435/7.1 |
| 6,288,215 B1 * | 9/2001 | Hsieh | 530/388.2 |
| 2003/0022248 A1 * | 1/2003 | Hsieh | G01N 33/6887 435/7.21 |
| 2004/0248322 A1 * | 12/2004 | Charlton | G01N 33/558 436/518 |
| 2012/0178910 A1 * | 7/2012 | Arunakumari | C07K 1/18 530/387.3 |

FOREIGN PATENT DOCUMENTS

| | | |
|---|---|---|
| JP | 2003-155297 | 5/2003 |
| JP | 2005-164583 | 6/2005 |
| JP | 2006-317226 | 11/2006 |
| JP | 2009-85911 | 4/2009 |

OTHER PUBLICATIONS

Lilley et al. "Two-dimensional gel electrophoresis: recent advances in sample preparation, detection and quantitation" (Curr Opin Chem Biol (2002) 6:46-50.*

Lambertz et al., Identification and Characterization of Pathogenic Yersinia enterocolitica Isolates by PCR and Pulsed-Field Gel Electrophoresis, Applied and Environmental Microbiology, Jul. 2005, pp. 3674-3681.*

* cited by examiner

*Primary Examiner* — Gary Counts
(74) *Attorney, Agent, or Firm* — Wenderoth, Lind & Ponack, L.L.P.

(57) ABSTRACT

A method for detecting pork in heated food by immunochromatographic detection with high performance and high sensitivity without causing non-specific reaction. The method provides a convenient and high-accuracy detection method using a polyclonal antibody. When a target to be detected in a sample, pork-derived protein in heat-processed food, is detected by immunochromatography, a polyclonal antibody specifically recognizing a protein of approximately 23 kD (molecular weight: 23000) contained in heat-treated pork is used as at least one or both detection antibodies.

9 Claims, 1 Drawing Sheet

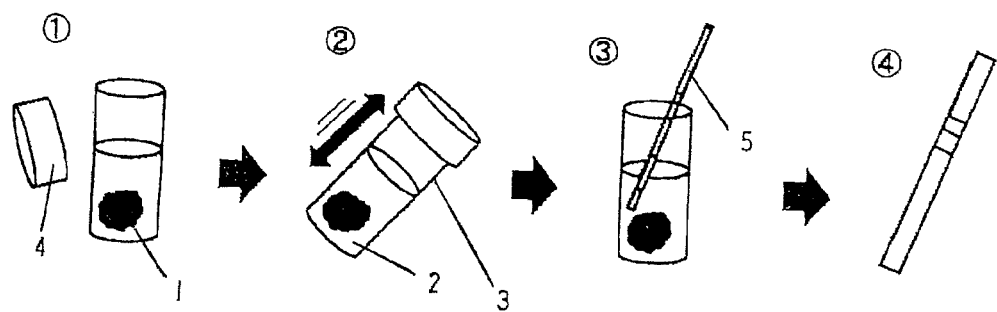

METHOD OF DETECTING PORK IN PROCESSED FOOD AND DETECTION KIT THEREFOR

This application is a U.S. national stage of International Application No. PCT/W2011/053438 filed Feb. 18, 2011.

TECHNICAL FIELD

The present invention relates to a method of detecting pork in processed food, in particular, in heat-treated processed food and a detection kit therefor. Furthermore, the present invention relates to a method of preparing a detecting antigen derived from animal species in processed food, in particular, in heat-treated processed food, and relates to an antibody obtained using the detecting antigen.

BACKGROUND ART

Since the EU Scientific Steering Committee stated their report on a risk of infection of bovine infectious diseases, such as bovine spongiform encephalopathy (BSE), to human being, use of meat-and-bone meal of BSE-infected cows as livestock feed has been acknowledged as a problem. In addition, issues of fake brand for branded beef and disguise of other meat to beef have raised awareness of general consumers.

At the same time, in patients with food allergy, various allergic symptoms, such as asthma, dermatitis, gastrointestinal dysfunction, and anaphylactic shock, are caused by food allergens contained in food. In some cases, the symptoms are serious. There is a tendency of an increase in number of food allergy patients, and consumers are highly interested in food safety.

As typical examples of food containing food allergens, generally well known are grain (e.g., buckwheat and wheat), eggs, meat (e.g., beef, pork, and chicken), fishes (e.g., mackerel and sardine), milk, shellfishes (e.g., crab), mollusks, beans (e.g., peanut and soybean), fruits (e.g., mango), and vegetables (e.g., garlic). Such food allergy-inducing food contains food allergy-inducing ingredients such as gluten, gelatin, casein, ovalbumin, ovomucoid, lysozyme, α-lactoalbumin, or β-lactoglobulin. Processed food contains many kinds of food and many kinds of food allergens, but currently there is no way to conveniently detect them.

In addition, in processed food (for example, by heating, pressurizing, enzyme treatment, freezing, drying, or salting), the protein ingredients in the food are denatured in their molecular structures or molecularly modified by the treatment. Therefore, in order to conveniently detect these ingredients in processed food, it is important to use appropriate antigens and epitopes for corresponding processed ingredients and non-processed raw ingredients, and researches and studies therefor have been conducted.

For example, a detection reagent that has been developed as a detection reagent for detecting a material in a sample, such as canned food or livestock feed, derived from animal tissue, represented by cow, hog, and chicken, heat-treated at a high temperature such as a temperature of higher than 100° C. includes a labeled antibody that is an antibody against serum albumin in a material derived from animal tissue heat-treated at a temperature not lower than 120° C. or its antigen-binding fragment labeled with a labeling agent and includes a carrier having a detection region where an antibody against serum albumin in a material derived from the animal tissue or its antigen-binding fragment is fixed. That is, it has been found that an antibody produced by an animal immunized with heat-denatured serum albumin protein as an immunogen specifically recognizes heat-denatured serum albumin and does not have a cross-reactivity with non-heated serum albumin, and proposed is a method (including immunochromatography) for detecting the presence of a heat-treated material derived from animal tissue in a sample (see Patent Literatures 1 and 2).

In addition, an IgE (immunoglobulin E) antibody obtained by immunizing an animal with a mixture (protein) of food allergens composed of non-denatured and/or denatured materials and a method of detecting a food allergen and food allergy-inducing food with the antibody are known (see Patent Literature 3).

Furthermore, it is known that pork in heat-treated food can be detected by ELISA (an immunological measurement method) using a monoclonal antibody produced by a deposited specific cell line (a cell line obtained by immunizing an animal with a specific protein in heated pork) (see Patent Literature 4).

Since this detection method uses a monoclonal antibody produced by a specific cell line (a cell line obtained by immunizing an animal with a specific protein in heated pork), the detection is accurate. However, the preparation of the monoclonal antibody is expensive, and, therefore, it is not suitable for applying to many patients in the medical field.

The present inventors performed a similar experiment by immunochromatography using a polyclonal antibody instead of the monoclonal antibody. The results showed insufficient accuracy due to cross-reactivity with materials other than pork, such as beef, in heated food.

Thus, it was observed that non-specific reaction occurred when pork in heated food, the object to be detected in a sample, was detected by immunochromatography using a polyclonal antibody. Therefore, there still remained a problem that non-specific reaction could not be sufficiently inhibited.

In addition, it is known that a surfactant such as TWEEN 20 or an inorganic salt such as sodium chloride is contained in a diluent that is used for diluting a sample when anallergen (protein) in food is detected by immunological measurement (see Patent Literature 5).

SUMMARY OF INVENTION

It is an object of the present invention to provide preparation of an ingredient derived from a specimen optimal for detecting by immunoassay pork in heated food with high performance and high sensitivity without causing non-specific reaction, a convenient and high-accuracy detection method using a polyclonal antibody obtained by using the ingredient, and a detection kit therefor.

Solution to Problem

The present invention relates to immunochromatographic detection of protein derived from pork in heat-processed food. The developer solution composition used in the present invention and the composition of chemical materials (other than biological materials) contained in the test kit are reagents widely used in conventional immunochromatography. For example, a developer solution is purified water or a buffer containing a nonionic surfactant (e.g., TWEEN 20 or TRITON-100), sodium chloride, and, according to circumstances, casein (powdered skim milk).

The present inventors have found a fact that a protein of approximately 50 kD (molecular weight: 50000) contained in raw pork, an extract extracted from raw pork, is surprisingly most suitable as an immunizing antigen for preparing an antibody used in a detection system for heated food.

Accordingly, the detection antibody (biological material) used in immunochromatographic detection according to the present invention for detecting a protein derived from pork in heat-processed food is particularly suitable for a detection system of heated food. The detection antibody differs from not only those used in immunochromatographic detection systems for proteins derived from pork in non-heated food, but also from detection antibodies (biological materials) used in conventionally known immunological detection of proteins derived from pork in heated-processed food. The present inventors have specified the detection antibody and have first completed the invention relating to a method of examining (detecting) the presence or absence of pork in heat-processed food by immunochromatography and an examination (detection) kit.

In the detection system for heated food according to the present invention, for example, a polyclonal antibody specifically recognizing a protein of approximately 23 kD (molecular weight: 23000) contained in pork heated at 100° C. or higher is preferably used as a detection antibody.

The present invention provides the following (a) to (e), a detection method, an antibody used therefor, a detection apparatus, and a detection kit:

(a) A first aspect of the present invention relates to a method for immunochromatographic detection of a protein derived from pork in heat-processed food using a polyclonal antibody as a detection antibody, wherein the polyclonal antibody is obtained by immunizing an animal with an immunizing antigen that is a protein having a molecular weight showing strong color development at approximately 50 kD (molecular weight: 50000) contained in an ion-exchange purified fraction of an extract extracted from raw pork belonging to a range of 40 kD (molecular weight: 40000) to 60 kD (molecular weight: 60000) when analyzed by Coomassie staining of sodium dodecyl sulfate-polyacrylamide gel electrophoresis (SDS-PAGE), and the polyclonal antibody specifically recognizes a protein of approximately 23 kD (molecular weight: 23000) belonging to a range of 20 kD (molecular weight: 20000) to 26 kD (molecular weight: 26000) contained in heat-treated pork.

(b) A second aspect of the present invention relates to a polyclonal antibody obtained by immunizing an animal with an immunizing antigen that is a protein having a molecular weight showing strong color development at approximately 50 kD (molecular weight: 50000) contained in an ion-exchange purified fraction of an extract extracted from raw pork belonging to a range of 40 kD (molecular weight: 40000) to 60 kD (molecular weight: 60000) when analyzed by Coomassie staining of sodium dodecyl sulfate-polyacrylamide gel electrophoresis (SDS-PAGE), wherein the polyclonal antibody specifically recognizes a protein of approximately 23 kD (molecular weight: 23000) belonging to a range of 20 kD (molecular weight: 20000) to 26 kD (molecular weight: 26000) contained in heat-treated pork.

(c) A third aspect of the present invention relates to an apparatus for immunochromatographic detection of a protein derived from pork in heat-processed food, the apparatus including a labeled material-holding portion holding a polyclonal antibody according to the second aspect labeled with a labeling material and a detection portion where a polyclonal antibody according to the second aspect is immobilized.

(d) A fourth aspect of the present invention relates to the apparatus for immunochromatographic detection according to the aspect (c), the apparatus being substantially composed of a sample application portion, a labeled material-holding portion, a chromatography medium, a detection portion, and an absorbing portion.

(e) A fifth aspect of the present invention relates to an immunochromatographic detection kit for detecting a protein derived from pork in heat-processed food, being substantially composed of a sample application portion, a labeled material-holding portion, a chromatography medium, a detection portion, and an absorbing portion, wherein the labeled material-holding portion holds a polyclonal antibody according to the second aspect labeled with a labeling material, and a detection portion is immobilized with a polyclonal antibody according to the second aspect.

Advantageous Effects of Invention

In the immunochromatographic detection of a protein derived from pork in heat-processed food according to the present invention, since a polyclonal antibody obtained by immunizing a rabbit or a goat (the animal is not limited thereto, other animals, that is, for example, horse, sheep, hog, chicken, mouse, rat, or guinea pig may be used) with a protein of approximately 50 kD (molecular weight: 50000) contained in raw pork, an extract extracted from raw pork, is used as the detection antibody (biological material), the detection is inexpensive compared to the case using a monoclonal antibody and is effective for many consumers, for example, for applying to many patients in the medical field.

In the present invention, since a protein of approximately 50 kD (molecular weight: 50000) contained in raw pork, an extract extracted from raw pork, is used as the antigen for immunizing an animal to obtain a polyclonal antibody to be used as a detection antibody (biological material), even though the antibody is polyclonal, there are no cross reaction not only with proteins derived from plants such as soybean but also with proteins derived from animals other than hog, such as cow, chicken, and sheep, and no reduction in sensitivity, and it is possible to accurately and easily determine the result of immunochromatographic detection of a protein derived from pork in heat-processed food.

The immunochromatographic detection of a protein derived from heat-treated pork according to the present invention can also be conveniently and inexpensively used for detecting a protein derived from pork contained not only in heat-processed food but also in health food, medicines, livestock feed, pet food, and so on that have been subjected to processing treatment (e.g., heating, heating/pressurizing, or drying) under temperature conditions that cause protein denaturation. Therefore, the present invention can contribute to solve problems of patients to whom pork causes allergy reaction or of general consumers who do not eat pork in terms of tastes or dietary cultures.

Since the immunochromatographic detection kit according to the present invention is a simpler device and can rapidly and inexpensively detect a protein derived from pork in heat-processed food, compared to PCR and ELISA methods, the kit has an advantage in which the device can contribute to the need of general consumers.

BRIEF DESCRIPTION OF DRAWINGS

FIG. 1 is a schematic diagram illustrating the use of an immunochromatographic detection kit according to the present invention.

DESCRIPTION OF EMBODIMENTS

The present invention will be described in detail below.

In the detection system for heated food according to the present invention, for example, a polyclonal antibody specifically recognizing a protein having a molecular weight of approximately 23 kD (molecular weight: 23000) contained in pork heated at 100° C. or higher is preferably used as a detection antibody.

In the immunochromatographic detection of a protein derived from pork in heat-processed food according to the present invention, a protein of approximately 50 kD (molecular weight: 50000) contained in raw pork, an extract extracted from raw pork, is used as an immunizing antigen, and a polyclonal antibody obtained by immunizing an animal (e.g., rabbit, goat, horse, sheep, hog, chicken, mouse, rat, or guinea pig) with the protein is used as a detection antibody (biological material).

The term "approximately 50 kD (molecular weight: 50000)" is an expression that does not particularly cause a technological problem for a person skilled in the art, but since the protein is a natural product having irregularity, especially, in order to quantitatively define it, it has been found that when proteins extracted from raw pork in an ion-exchange column purified fraction are subjected to sodium dodecyl sulfate-polyacrylamide gel electrophoresis and then analyzed by Coomassie staining (SDS-PAGE analysis), a major characteristic protein of raw pork has a molecular weight of mainly 50 kD (molecular weight: 50000), which can be experimentally defined to be entirely included in the range of about 40 kD (molecular weight: 40000) to 60 kD (molecular weight: 60000), that is, the majority of a protein of "approximately 50 kD (molecular weight: 50000)" is present at high concentration in the range of fractions 1 to 5, and it can be assumed that the protein is present not only as a monomer but also as polymers such as a dimer or a trimer, but at least in this molecular weight analysis, a protein having a molecular weight of "approximately 50 kD" is the major protein that is characteristic in pork and is suitable as an immunizing antigen.

In the present invention, the protein of approximately 50 kD (molecular weight: 50000) contained in raw pork is preferably used as an immunizing antigen. The immunizing antigen may be only a protein fraction showing a molecular weight of approximately 50 kD by analysis such as polyacrylamide gel electrophoresis or may be protein groups mainly containing a protein fraction showing a molecular weight of approximately 50 kD.

Furthermore, in the present invention, since a protein of approximately 50 kD (molecular weight: 50000) contained in raw pork, an extract extracted from raw pork, is used as the antigen for immunizing an animal to obtain a polyclonal antibody to be used as a detection antibody (biological material), there are no cross reaction not only with proteins derived from plants such as soybean but also with proteins derived from animals other than hog, such as cow, chicken, and sheep, and no reduction in sensitivity, and excellent performance is achieved in accurate and easy determination of the result of immunochromatographic detection of the protein derived from pork in heat-processed food.

Furthermore, in the present invention, a method of recognizing processed pork relatively easily and accurately has been investigated. As a result, a relationship between characteristics of the protein to be recognized and the recognizing antibody has been pursued by paying attention to the protein contained in processed pork, and it has been found that the protein contained in processed pork to be specifically recognized is a protein of approximately 23 kD (molecular weight: 23000), as an experimentally defined range, when the molecular weight was determined by Western Blotting analysis (hereinafter abbreviated to "WB analysis").

On the basis of the characteristic that meat is all natural protein, it is easily predicted that the molecular weights of proteins constituting processed meat range from low to ultra-high. Proteins extracted from various kinds of processed meat were subjected to electrophoresis, and then proteins having molecular weights in the range of 0 kD (molecular weight: 0) to about 250 kD (molecular weight: 250000) were subjected to WB analysis using a polyclonal antibody obtained by immunizing an animal with a protein contained in raw pork and having of approximately 50 kD (molecular weight: 50000) as an immunizing antigen. As a result, strongly recognized is a porcine protein mainly of 23 kD (molecular weight: 23000), which is experimentally defined to be within a range of approximately 20 kD (molecular weight: 20000) to 26 kD (molecular weight: 26000), that is, a molecular weight of "approximately 23 kD (molecular weight: 23000)", and proteins other than porcine protein, that is, proteins of cow, sheep, and chicken were not recognized. The proteins extracted from various kinds of processed meat were subjected to electrophoresis and then to WB analysis using a monoclonal antibody recognizing porcine troponin I gave the similar results to those of the present invention.

In the present invention, when it is mentioned that a porcine protein of approximately 23 kD is recognized, the term "approximately 23 kD" specifies the molecular weight of a protein according to a common measuring method as the molecular weight of the protein in detection of processed pork. The specific value of 23 kD highly effectively functions without particular problems in the handling of the protein for detection. It merely defines as a protein of approximately 23 kD and is an expression in accordance with the molecular weight that can be sufficiently effectively measured and recognized by a person skilled in the art in the detection of processed pork. In order to quantitatively express the term "approximately 23 kD", since the processed meat is a natural product having irregularities in molecular weight, structure, and so on, as a possible numerical value range, the expression that the majority of a protein having a molecular weight belongs to the range of about 20 to 26 kD can be a more clear quantitative expression. At least, the detection method of the present invention can be accurately performed by merely specifying the protein having a molecular weight of approximately 23 kD by WB analysis. The finding that the polyclonal antibody produced by the inventors specifically recognizes the protein of approximately 23 kD in processed pork and the construction of the easy, rapid, and inexpensive detection method in accordance with this principle is based on the knowledge of the present inventors.

The composition of a developer solution and the composition of chemical components (other than biological materials) included in the test kit according to the present invention are the same as reagents widely used in conventional immunochromatography. As the reagents for immunochromatography, various chemical materials, such as a buffer, a nonionic surfactant, according to circumstances, a chelating agent, can be used for achieving their functions and purposes.

The buffering agent contained in the immunochromatographic reagent composition, such as an extraction developer solution, of the present invention is not particularly limited as long as it can achieve the function (buffering function) without being significantly affected by a change in concentration due to addition of a sample or evaporation or dilution of the sample or contamination with a slight amount of foreign substances from the outside.

Examples of the buffering agent in the present invention include acetate buffers (acetic acid and sodium acetate), phosphate buffers (phosphoric acid and sodium phosphate), citrate buffers (citric acid and sodium citrate), borate buffers, Tris hydrochloride buffers (Tris(hydroxylmethyl)aminomethane and hydrochloric acid), TE buffers (Tris and ethylenediamine tetraacetic acid), TAE buffers (Tris, acetic acid, and ethylenediamine tetraacetic acid), TBE buffers (Tris, boric acid, and ethylenediamine tetraacetic acid), and HEPES buffers (2-[4-(2-hydroxyethyl)-1-piperazinyl]ethane sulfonic acid). Preferred are acetate buffers, phosphate buffers, Tris hydrochloride buffers, and HEPES buffers.

The concentration of the buffering agent contained in the immunochromatographic reagent composition of the present invention is in a range of 0.01 to 250 mM, preferably in a range of 10 to 200 mM, and more preferably in a range of 30 to 180 mM. A concentration of smaller than 0.01 mM is insufficient for buffering. A concentration of larger than 250 mM is unnecessarily high and is economically wasteful.

Examples of the nonionic surfactant that can be contained in the immunochromatographic reagent composition of the present invention include polyoxyethylene alkyl ethers, polyoxyethylene/polyoxypropylene alkyl ethers, polyoxyethylene sorbitan fatty acid esters (trade name: "TWEEN" series), polyoxyethylene p-t-octylphenyl ethers (trade name: "TRITON" series), polyoxyethylene p-t-nonylphenyl ethers (trade name: "TRITON N" series), alkyl polyglucosides, fatty acid diethanolamide, and alkyl monoglyceryl ethers. The nonionic surfactants may be used alone or as a mixture of two or more.

The content of the nonionic surfactant in the immunochromatographic reagent composition of the present invention is in a range of 0.01 to 10% by weight, preferably in a range of 0.05 to 5% by weight to the immunochromatographic reagent composition. A content of less than 0.05% by weight is insufficient for inhibiting non-specific reaction, resulting in inaccurate determination. A content of higher than 10% by weight is unnecessarily high, which does not advantageously affect inhibition of non-specific reaction and is also economically wasteful.

The nonionic surfactant can be optionally used together with, for example, another nonionic surfactant or ionic surfactant.

The chelating agent contained, according to need, in the immunochromatographic reagent composition of the present invention is not particularly limited as long as it can function as a ligand having a plurality of coordination positions.

Examples of the chelating agent in the present invention include ethylenediamine, dipyridine, ethylenediamine tetraacetic acid (hereinafter referred to as "EDTA"), EDTA.2Na, EDTA.3Na, EDTA.4Na, EDTA derivatives (e.g., EDTA.2NH$_4$, EDTA.3K, EDTA.special amine salt), EDTA metal salts (e.g., EDTA.Ca.2Na), hydroxyethylethylenediamine triacetic acid (HEDTA) systems, dihydroxyethylethylenediamine diacetic acid (DHEDDA) systems, 1,3-propanediamine tetraacetic acid (1,3-PDTA) systems, diethylenetriamine pentaacetic acid (DTPA) systems, triethylenetetramine hexaacetic acid (TTHA) systems, nitrilotriacetic acid (NTA) systems, gluconic acid systems, hydroxyethylimino diacetic acid (HIMDA) systems, L-aspartic acid-N,N-diacetic acid (ASDA) systems, aminotrimethylenephosphonic acid (NTMP) systems, hydroxyethanephosphonic acid (HEDP) systems, tetrasodium 3-hydroxy-2,2'-iminodisuccinate, phenanthroline, porphyrin, and crown ether.

The concentration of the chelating agent contained, according to need, in the immunochromatographic reagent composition of the present invention is in a range of 0.01 to 10 mM, preferably in a range of 0.1 to 5 mM, and more preferably in a range of 0.5 to 2 mM. A concentration of smaller than 0.01 mM is insufficient for inhibiting non-specific reaction, resulting in inaccurate determination. A concentration of larger than 10 mM is unnecessarily high and is economically wasteful.

The immunochromatographic reagent composition of the present invention may further contain additives that are known to inhibit side reaction based on biological affinity or inhibit non-specific reaction, for example, proteins (e.g., bovine serum albumin, casein, or gelatin), polymers (e.g., polyethylene glycol, methylcellulose, polyvinylpyrrolidone, polyvinyl alcohol, or dextran), or ionic surfactants or polyanions (e.g., dextran sulfate, heparin, polystyrene sulfonic acid, or chondroitin sulfate) that enhance antigen-antibody reaction or inhibit non-specific reaction, and preservatives or antimicrobials. These additives may be used alone or in combination, and such a use is possible and effective without any restriction. Furthermore, one or more of these proteins, polymers, ionic surfactants or polyanions that enhance antigen-antibody reaction or inhibit non-specific reaction, and the preservatives or antimicrobials may be held on the mobile path of the mobile phase on a chromatographic medium constituting the stationary phase, and such a use is possible and effective without any restriction.

In an embodiment of use of the immunochromatographic reagent composition in the present invention, the composition can be held in a sample pad (sample application portion) in an immunochromatography apparatus by applying the composition to the sample pad or immersing the sample pad in the composition and then drying the sample pad. In another embodiment, the immunochromatographic reagent composition in the present invention is held on a chromatography medium by providing an additive-holding portion at an appropriate place between an end of the sample application portion and an absorbing portion and letting the composition to be held there. For example, the application area of the composition may be near the sample application portion or the labeled material-holding portion or its vicinity. In particular, an embodiment in which the composition is held on only the sample application portion and/or labeled material-holding portion is preferred.

The method of using the immunochromatographic reagent composition of the present invention is not limited to the above-mentioned embodiments, and the composition may be used as an extraction developer solution or a diluent for samples. For example, the extraction developer solution of the present invention is ultrapure water or a buffer containing a nonionic surfactant (e.g., TWEEN 20 or TRITON-100), sodium chloride, and, according to circumstances, casein (powdered skim milk), etc.

As the extraction developer solution, usually, water is used as a solvent, and a buffer, a nonionic surfactant, protein, and a polymer, and, according to need, a chelating agent are added to the solvent. The addition order is not particularly limited, and they may be added at once. When the composition is used as an extraction developer solution, the form of the extraction developer solution can be optimized depending on the state, such as solid or paste, of the sample for the detection. A sample for the detection may be mixed with the developer solution in advance, and the mixture may be supplied/dropped onto the sample pad (sample application portion) for development, or the sample may be supplied/dropped onto the sample pad (sample application portion) in advance, and then the developer solution may be supplied/dropped onto the sample pad (sample application portion). When the composition is used as a diluent for diluting samples, a sample diluted with the diluent can be used by being directly supplied/dropped onto the sample pad (sample application portion).

Typical examples of the sample (specimen) containing the object to be detected of the present invention include food and health food that are treated mainly for heat processing or sterilization treatment at a temperature at which proteins are denatured, but the sample is not limited thereto, and livestock feed and medicines also can be used as samples (specimens).

In the present invention, a protein of approximately 50 kD (molecular weight: 50000) contained in raw pork is preferably used as an immunizing antigen. The immunizing antigen may be only a protein fraction shown near 50 kD in an analysis method such as polyacrylamide gel electrophoresis or may be protein groups mainly containing a protein fraction shown near 50 kD.

A preparation process of the immunizing antigen of the present invention is as follows:
Reagent: amount used per 1 kg of meat
  Sodium chloride: 0.14 M aqueous solution, 2 L
  Sodium acetate: 1 M aqueous solution, 200 mL 0.1 M aqueous solution, 500 mL
  Ammonium sulfate: 2872 g
  1 N hydrochloric acid: moderate (rough standard: 250 mL)
  Polyethylene glycol 20000: 30% aqueous solution, 1 L
  Sodium acetate buffer (pH=3.7): 0.1 M solution, 3.2 L
Devices
  Scissors, tweezers (for treatment of meat)
  Beaker
  Food processor
  Ultrasound homogenizer
  Centrifuge and centrifuge tube (Kokusan centrifuge)
  Suction filtration equipment (suction bottle, Buchner funnel)
  Magnetic stirrer
  pH meter
  dialysis membrane (used after boiling for removing glycerol and sulfur)
  AKTA (protein purifying apparatus)
Operating Procedure
I. Removal of Protein Other than Antigen (1) Fat removed lean meat (fillet pork) (500 g) is minced with a food processor, followed by addition of a 0.14 M aqueous solution of sodium chloride (1 L) thereto. The resulting mixture is dispersed with an ultrasound homogenizer to produce slurry. The slurry is incubated at room temperature for 1 hour, followed by centrifugation (10000 g, 4° C., 20 min). The supernatant was filtered through Kimwipes, followed by suction filtration through Whatman No. 42 filter paper. The supernatant is diluted with IEW to 1900 mL, and a 1 M aqueous solution of sodium acetate (100 mL) is added thereto. Ammonium sulfate (722 g) is added thereto with stirring on ice, and the resulting mixture is stirred on ice (4° C.) for 2 hours and then incubated at 4° C. overnight.

(2) The precipitate is sufficiently stirred and subjected to centrifugation (10000 g, 4° C., 20 min). The supernatant is collected (discard the pellet), and then a 1 N hydrochloric acid is added to the supernatant to adjust the pH to 4.9. The resulting mixture is incubated at 4° C. overnight.

(3) The precipitate is sufficiently stirred and subjected to centrifugation (10000 g, 4° C., 20 min). The supernatant is collected (discard the pellet), and then a 1 N hydrochloric acid is added to the supernatant to adjust the pH to 3.7. The resulting mixture is incubated at 4° C. overnight.

(4) After centrifugation (10000 g, 4° C., 20 min), the supernatant is collected (discard the pellet). Ammonium sulfate (714 g) is gradually added to the supernatant with stirring on ice, and the resulting mixture is stirred at 4° C. for 2 hours and then incubated at 4° C. overnight.

(5) The supernatant by centrifugation (19000 g, 4° C., 20 min) is removed, and the pellet is suspended in 120 mL of sterilized purified water. The suspension is incubated at 4° C. overnight.

(6) The supernatant by centrifugation (19000 g, 4° C., 20 min) is fractionated in dialysis membrane and subjected to dialysis with 2 to 3 L of sterilized purified membrane, followed by dialysis with 2 to 3 L of sterilized purified membrane.

(7) The dialyzed solution is dialyzed with 1 to 2 L of a 30% aqueous solution of PEG 20000 and is concentrated to 40 mL. The concentrated solution is dialyzed with a 0.01 M acetate buffer (pH 3.7, 2000 mL) and with another 0.01 M acetate buffer (pH 3.7, 2000 mL).

II. Purification of Antigen

The antigen obtained by the above (1) to (7) is purified by the following procedure:

(8) The dialyzed solution in the above (7) is centrifuged (10000 g, 4° C., 20 min), and the supernatant is purified using a cation-exchange column. The buffer used for the first column equilibration and column washing is a 0.01 M acetate buffer (pH 3.7), and the buffer used for sample elution and column washing immediately after the elution is a 0.8 M aqueous solution of sodium acetate (pH 3.7). Fractions f1 to f10 are obtained as cation-exchange purified fractions.

(9) A fraction of the major peak part (fraction showing highest protein concentration in UV spectrum) is collected. The fraction is dialyzed with an approximate amount of PBS (0.01 M phosphate buffered saline) and then with a 30% aqueous solution of PEG 20000 (1000 mL) to concentrate to 2 mg protein/mL.

(10) Fractions f1 to f5 are collected and are subjected to quantitative determination of protein (protein assay). By the above-described procedure, an immunizing antigen is prepared from raw pork.

The ion-exchange purified fractions f1 to f10 are subjected to sodium dodecyl sulfate-polyacrylamide gel electrophoresis (SDS-PAGE) (150 V, 45 to 55 min), and then protein is stained by Coomassie staining. The fractions f1 to f5 show strong bands near 50 kD (molecular weight: 50000).

The ion-exchange purified fractions f1 to f10 are subjected to sodium dodecyl sulfate-polyacrylamide gel electrophoresis (SDS-PAGE) (150 V, 45 to 55 min) and then Western Blotting (15 V, 60 min) analysis using a polyclonal antibody produced by Tanaka Kikinzoku Kogyo K.K. The fractions f1 to f5 show strong bands near 50 kD.

Preparation of Polyclonal Antibody

Rabbit is immunized with the immunizing antigen prepared from raw pork as in above in accordance with a common method to obtain antiserum. A polyclonal antibody is purified from the antiserum by a procedure including dialysis with 50% saturated ammonium sulfate and then purification and collection with a DEAE column (anion-exchange column).

Commercially available four kinds of meat (pork, beef, mutton, and chicken) are heated at 100° C. and are subjected to Western Blotting analysis using the polyclonal antibody produced by Tanaka Kikinzoku Kogyo K.K. to detect a band that strongly recognized pork-derived protein near 23 kD (molecular weight: 23000). It was recognized that this antibody had high specificity to hog, compared to various kinds of meat other than pork. In addition, it was confirmed by Western Blotting analysis that this polyclonal antibody recognized protein near 50 kD contained in raw pork. Thus, it was revealed that the protein near 50 kD contained in raw pork is suitable for an immunizing antigen of the present invention.

The structure of an immunochromatography apparatus or a detection kit according to the present invention will be described below.

The sample application portion is configured of a porous sheet having characteristics to rapidly absorb a sample, but hardly hold it, to allow the sample to rapidly penetrate to a reaction portion. Examples of the porous sheet include cellulose filters, glass filters, polyurethane, polyacetate, cellulose acetate, nylon, and cotton fabric. In an embodiment of the present invention, in order to inhibit non-specific reaction, the immunochromatographic reagent composition containing additives such as a buffer, a nonionic surfactant, and protein, and according to need, a chelating agent may be held in the sample pad (sample application portion) by previously impregnating the sample pad with the immunochromatographic reagent composition and then, for example, drying it.

The labeled material-holding portion is configured so as to hold a labeled reagent composed of a labeling component and a reagent component labeled with the labeling component. Examples of the labeling component that can be used include metal colloidal particles such as gold colloidal particles and silver colloidal particles, colored latex particles obtained by dyeing synthetic polymer synthesized by (co)polymerization of various monomers, enzymes, fluorescent compounds, and other materials. Among them, gold colloidal particles show strong color development, are easily produced, and can be simply applied to labeling, and are therefore preferably used. The size of the gold colloidal particles is 1 to 500 nm, preferably 10 to 250 nm, and more preferably 30 to 100 nm. The reagent component is particles or molecules having an ability of recognizing an analyte and is a monoclonal antibody, a polyclonal antibody, or a fragment thereof (second reagent).

The chromatographic medium is composed of a membrane carrier and a detection portion (or referred to as "reaction portion") formed on the membrane carrier. The membrane carrier is not particularly limited as long as it can absorb and transfer a sample by a capillary action. For example, the chromatographic medium is selected from the group consisting of nitrocellulose, cellulose acetate, nylon, polyether sulfone, polyvinyl alcohol, polyester, glass fiber, polyolefin, cellulose, and artificial polymers composed of mixed fibers thereof. The detection portion has a polyclonal antibody or its fragment (first reagent) immobilized on a nitrocellulose sheet.

The absorbing portion is made of a material having an ability of rapidly absorbing an excessive sample, such as a glass filter.

A backing sheet is a base material. One surface of the backing sheet is provided with adhesion by application of an adhesive or attachment of adhesive tape, and on the adhesive surface, the sample application portion, the labeled material-holding portion, the chromatographic medium (having the detection portion), and a part of or the whole absorbing portion are adhesively disposed. The backing sheet is not particularly limited as the base material as long as it is impermeable for a sample solution and for moisture by the adhesive.

One of or both the reagent component (first reagent) used in the detection portion (or referred to as "reaction portion") and the reagent component (second reagent) used in the labeled material-holding portion is a polyclonal antibody, and in consideration of manufacturing cost and stable supply of the antibody while maintaining the specificity, a polyclonal antibody can be used as both reagent components.

The monoclonal antibody and polyclonal antibody or their fragments can be prepared by a known method. Common examples of the antibody-producing animal include rabbit, goat, mouse, and rat.

The monoclonal antibody is prepared through a common method by hybridizing myeloma cells with spleen cells of a mouse immunized with an antigen (protein of approximately 50 kD (molecular weight: 50000) contained in raw pork, an extract extracted from raw pork), selecting a hybridoma producing a target antibody, and collecting the monoclonal antibody produced by the hybridoma. For example, see the method of Kohler and Milstein (Nature, 256 (1975), pp. 495-497).

The polyclonal antibody is basically prepared through a common method by separating a target antibody from antiserum obtained by immunizing an antibody-producing animal (e.g., rabbit, goat, mouse, rat, horse, hog, or chicken) with an antigen (protein of approximately 50 kD (molecular weight: 50000) contained in raw pork, an extract extracted from raw pork). For example, see the literature by Berger, et al. (J. Assoc. Off. Anal. Chem., vol. 71, no. 2, 1988).

The principle of judgment will be roughly described below:

1. A predetermined amount (usually 0.1 to 2 mL) of a sample (for example, an extraction developer solution of heat-processed food containing meat) is dropped onto a sample pad. The sample applied onto the sample pad moves in the sample pad. When the sample pad is impregnated with a specific immunochromatographic reagent composition, the immunochromatographic reagent composition is dissolved in the moisture content of the sample and moves together with the sample.

2. The sample (for example, the extraction developer solution of heat-processed food containing meat) or the sample dissolving the immunochromatographic reagent composition first moves to the labeled material-holding portion. During passing of the sample through the labeled material-holding portion, the labeling reagent (second reagent) being held at the labeled material-holding portion is dissolved in the moisture content of the sample to move together with the sample.

3. Then, the labeling agent dissolved in the moisture content of the sample passes through the detection portion on the chromatography medium. When the sample contains pork, the antigen in the pork specifically reacts with the antibody held, that is, immobilized on the detection portion and the labeled reagent to form a sandwich-like complex by antigen-antibody specific binding reaction, resulting in coloring in the detection portion. When the sample does not contain pork, the labeling agent dissolved in the moisture content of the sample, even if the sample passes through the detection portion on the chromatography medium, specific binding reaction does not occur. Therefore, the detection portion is not colored.

4. Lastly, the moisture content of the sample moves to the absorbing portion.

Thus, the presence or absence of pork in a sample can be exactly determined.

EXAMPLE

The immunochromatography apparatus that is used in the present invention will be described in detail below, but it is merely an example, and the present invention is not limited thereto.

1. Production of a Reaction Portion on a Chromatography Medium

An anti-pork polyclonal antibody, diluted with 2% StabiliGuard (SurModics), 5% isopropyl alcohol, and a carbonate buffer (pH 9.0) to a concentration of 0.65 mg/mL, was applied onto a 25×2.5 cm nitrocellulose membrane (manufactured by Millipore, HF120) with an antibody coating machine (manufactured by BioDot), followed by drying at 40 to 50° C. for 60 minutes and then at room temperature overnight to produce a reaction portion on the chromatography medium.

2. Production of Labeling Material Solution

Anti-pork polyclonal antibody was diluted with an HEPES buffer (pH 8.5) to a concentration of 0.02 mg/mL. The diluted anti-pork polyclonal antibody (0.1 mL) was added to a gold colloidal suspension (manufactured by Tanaka Kikinzoku Kogyo K.K., 0.5 mL, average particle diameter: 60 nm), and the resulting mixture was left to stand at room temperature for 10 minutes. Subsequently, CE510 (JSR Corporation, 0.1 mL) and then 0.05 mL of 1% polyethylene glycol dissolved in a potassium phosphate solution (pH 7.5) were added thereto, followed by sufficient stirring. The mixture was left to stand at room temperature for 10 minutes and then centrifuged at 8000×g for 15 minutes. The supernatant was removed, and a buffer (pH 7.4) containing 1% by weight of bovine serum albumin (0.1 mL) was added to the residue to obtain a labeling material solution.

3. Production of Chromatography Medium

The above-produced labeling material solution was uniformly applied onto a glass fiber pad, and the pad was dried with a vacuum dryer to obtain a detection reagent holding member. Then, the above-prepared chromatography medium having the reaction portion, detection reagent holding member, a sample pad to be used as a portion to which a sample is applied, and an absorbing pad for absorbing the applied sample and an insoluble carrier were bonded to a base material of a backing sheet. Lastly, by bonding of a laminate seal and cutting to a width of 5 mm with a cutter, chromatography medium was obtained.

4. Preparation of Extraction Developer Solution Skim milk, TWEEN 20, sodium chloride were added to a HEPES buffer (pH 8.0) to obtain concentrations of 0.2%, 0.15%, and 0.05 M, respectively, and sodium azide serving as a preservative was further added thereto to obtain a concentration of 0.1%, followed by mixing.

5. Production of Sample

To 0.5 mL of the extraction developer solution, 0.1 to 0.2 g of processed pork or processed meat derived from an animal other than hog was added, and the mixture was shaken for 30 seconds by hand.

6. Measurement

The presence or absence of pork in a sample was measured using the above-produced chromatography medium according to the following process. The above-produced sample containing pork was defined as a positive specimen, the above-produced sample containing meat derived from an animal other than hog was defined as a negative specimen, and the end of the chromatography medium was immersed in any of the sample solutions. After confirmation of flowing out of the gold colloid from the glass fiber pad, the immersed chromatography medium was taken out from the solution and was placed on a horizontal table. After 10 to 15 minutes, the result was visually judged.

A test method for the presence or absence of pork in test food using the above-produced chromatography apparatus (test kit) is shown in FIG. 1. The test method is conducted by the following procedures 1 to 5:

1. Add food (about 0.1 to 0.2 g) to be tested to a tube containing the above-described extraction developer solution (0.5 mL).
2. Tightly cover the tube with the lid, and shake the tube for about 30 seconds by the hand.
3. Take off the lid, immerse the end of the sample application portion of the test kit in the solution, and confirm that a red solution is developed on the test kit.
4. After confirmation of infiltration of the red solution, take out the test kit, and place it on a horizontal table.
5. After 10 to 15 minutes, confirm the presence or absence of a line.

Test examples of the present invention will be described below, but the present invention is not limited thereto. Visual judgment was performed 10 minutes after the dropping of samples, and a sample that showed a red line at the detection portion was defined as "+", a sample that showed that a line more clearly in a strong (deep color) state was defined as "++", a sample that showed a line in a significantly strong state was defined as "+++", a sample that did not show a red line was defined as "−", and a sample that showed a line in a weak (faint color) state was defined as (±).

Test Example 1

As processed test food, beef containing pork at a ratio (pork/beef) of 0% by weight, 0.1% by weight, 0.5% by weight, 1% by weight, or 5% by weight was evaluated. The results are show in Table 1.

In production Lot Nos. 1 to 3, evaluation was conducted using a polyclonal antibody obtained by immunizing a rabbit with an extract (protein) obtained from raw pork as the detection reagent.

The results showed that pork contained in beef at a concentration of 0.1% by weight or more could be detected without non-specific reaction (false positive). In this Test Example, lot-to-lot difference and variation in repeated tests did not occur.

In Comparative Example, the same detection as the Test Example was conducted using a polyclonal antibody obtained by immunizing a rabbit with an extract (protein) obtained by heat-treating raw pork.

The results showed non-specific reaction (false positive). Beef was also detected, showing a decrease in specificity to pork.

TABLE 1

Detection of pork in processed meat (heated food)

| Production Lot. No. | N = 3 | % by weight (pork/beef) | | | | |
| --- | --- | --- | --- | --- | --- | --- |
| | | 0 | 0.1% | 0.5% | 1% | 5% |
| 1 | 1 | − | + | ++ | +++ | +++ |
| | 2 | − | + | ++ | +++ | +++ |
| | 3 | − | + | ++ | +++ | +++ |

TABLE 1-continued

Detection of pork in processed meat (heated food)

| Production | | % by weight (pork/beef) | | | | |
|---|---|---|---|---|---|---|
| Lot. No. | N = 3 | 0 | 0.1% | 0.5% | 1% | 5% |
| 2 | 1 | − | + | ++ | +++ | +++ |
|   | 2 | − | + | ++ | +++ | +++ |
|   | 3 | − | + | ++ | +++ | +++ |
| 3 | 1 | − | + | ++ | +++ | +++ |
|   | 2 | − | + | ++ | +++ | +++ |
|   | 3 | − | + | ++ | +++ | +++ |
| Comparative | 1 | + | + | ++ | +++ | +++ |
| Example 1 | 2 | + | + | ++ | +++ | +++ |
|   | 3 | + | + | ++ | +++ | +++ |

Test Example 2

As processed test food, chicken containing pork at a ratio (pork/chicken) of 0% by weight, 0.25% by weight, 0.5% by weight, 1% by weight, or 5% by weight was evaluated. The results are show in Table 2.

In production Lot Nos. 1 to 3, evaluation was conducted using a polyclonal antibody obtained by immunizing a rabbit with an extract (protein) obtained from raw pork as the detection reagent.

The results showed that pork contained in chicken at a concentration of 0.25% by weight or more could be detected without non-specific reaction (false positive). In this Test Example, lot-to-lot difference and variation in repeated tests did not occur.

TABLE 2

| Production | | % by weight (pork/chicken) | | | | |
|---|---|---|---|---|---|---|
| Lot. No. | N = 3 | 0 | 0.25% | 0.5% | 1% | 5% |
| 1 | 1 | − | + | ++ | ++ | +++ |
|   | 2 | − | + | ++ | ++ | +++ |
|   | 3 | − | + | ++ | ++ | +++ |
| 2 | 1 | − | + | ++ | ++ | +++ |
|   | 2 | − | + | ++ | ++ | +++ |
|   | 3 | − | + | ++ | ++ | +++ |
| 3 | 1 | − | + | ++ | ++ | +++ |
|   | 2 | − | + | ++ | ++ | +++ |
|   | 3 | − | + | ++ | ++ | +++ |

Test Example 3

The detection kit of the present invention was evaluated by measuring extraction solutions extracted from heated single food (100%) of pork, beef, chicken, lamb, or soybean. The results are shown in Table 3.

The results showed that only protein derived from pork was detected, whereas proteins extracted from beef, chicken, lamb, or soybean were not detected, clearly showing specificity to pork. In also this Test Example, lot-to-lot difference and variation in repeated tests did not occur.

TABLE 3

Specificity confirming test (single heat-processed food)

| Production Lot. No. | N = 3 | Pork | Beef | Chicken | Lamb | Soybean |
|---|---|---|---|---|---|---|
| 1 | 1 | +++ | − | − | − | − |
|   | 2 | +++ | − | − | − | − |
|   | 3 | +++ | − | − | − | − |
| 2 | 1 | +++ | − | − | − | − |
|   | 2 | +++ | − | − | − | − |
|   | 3 | +++ | − | − | − | − |
| 3 | 1 | +++ | − | − | − | − |
|   | 2 | +++ | − | − | − | − |
|   | 3 | +++ | − | − | − | − |

Test Example 4

Comparison between the detection kit (immunochromatography) of the present invention and PCR method Material descriptions (pork, beef, or chicken) of commercial heated food products were judged by the detection kit of the present invention using extracts from the heated food products as detection samples. The same judgment was also conducted by a PCR method, which is known as a genetic method, instead of the detection kit of the present invention, using extracts from the heated food products as detection samples. The results are shown in Table 4.

The results of the detection kit of the present invention by immunochromatography were approximately the same as those of detection by the PCR method. Food products having a label indicating the presence of pork were detected by both methods. Proteins extracted from beef and chicken were not detected, and only pork-derived protein was detected. This result clearly shows specificity to pork. It was revealed from the results that the test kit of the present invention by immunochromatography can specifically detect pork contained in heated food products with accuracy that is not inferior to the PCR method, which is known to have high specificity and high performance.

TABLE 4

| Food | Material description | Country of manufacture | PCR data | Data of kit of the present invention |
|---|---|---|---|---|
| Beef curry | Beef | Japan | − | − |
| Chicken curry | Chicken | Japan | − | − |
| Argentina beet loaf | Beef | Philippines | − | − |
| Argentina carne norte | Chicken | Philippines | − | − |
| Argentina corn beef | Beef | Philippines | − | − |
| Swift Juicy carne | Chicken | Philippines | − | − |
| Corn beef | Beef | China | − | − |
| Pork luncheon meat | Pork | China | + | + |
| Curry corn beef | Beef | China | − | − |

INDUSTRIAL APPLICABILITY

The detection kit of the present invention is based on immunochromatography and, therefore, can be widely used in the field to which immunological assay is applied by using the antigen and antibody of the present invention immobilized on an insoluble carrier. Since the presence or absence of pork in heat-processed food can be conveniently, rapidly, and specifically detected, the present invention can contribute to solve problems of patients to whom pork causes allergy reaction or of general consumers who do not eat pork in terms of tastes or dietary cultures. The immunochromatographic detection of the present invention can be conducted conveniently, rapidly, and inexpensively, compared to PCR and ELISA methods, and therefore has high industrial applicability.

REFERENCE SIGNS LIST

1 Test food
2 Extraction developer solution
3 Tube
4 Lid
5 Detection chip

CITATION LIST

Patent Literature

PTL 1: JP-A-2006-317226
PTL 2: JP-A-2005-164583
PTL 3: JP-A-2003-155297
PTL 4: U.S. Pat. No. 6,288,215
PTL 5: JP-A-2009-085911

The invention claimed is:

1. A method for detecting the presence of pork in a heat-processed food comprising
obtaining one or more immunizing antigens from raw fillet pork by preparing a slurry of minced raw fillet pork and removing proteins other than the one or more immunizing antigens from the slurry of minced raw fillet pork by precipitation and centrifugation, and then purifying the one or more immunizing antigens using a cation-exchange column to obtain the one or more immunizing antigens being proteins having molecular weights showing color development at approximately 50 kD in an ion-exchange purified fraction of an extract extracted from the raw fillet pork when analyzed by Coomassie staining of sodium dodecyl sulfate-polyacrylamide gel electrophoresis, wherein the raw fillet pork is not heat treated,
immunizing an animal with the one or more immunizing antigens,
obtaining one or more polyclonal antibodies from the animal that was immunized with the one or more immunizing antigens,
detecting the presence of pork in the heat-processed food by using the one or more polyclonal antibodies as detection antibodies to detect the presence of one or more porcine proteins contained in heat-treated pork having a molecular weight of approximately 23 kD, wherein proteins other than porcine proteins are not detected,
wherein the pork in the heat-processed food is heated to 100° C. or higher.

2. The method for detecting the presence of pork in a heat-processed food according to claim 1, wherein the animal is selected from the group consisting of a rabbit, a goat, a horse, a sheep, a hog, a chicken, a mouse, a rat, and a guinea pig.

3. The method for detecting the presence of pork in a heat-processed food according to claim 1, wherein the heat-processed food is selected from the group consisting of livestock feed and pet food.

4. The method for detecting the presence of pork in a heat-processed food according to claim 1, wherein the one or more polyclonal antibodies do not cross-react with proteins derived from plants and animals other than hog.

5. The method for detecting the presence of pork in a heat-processed food according to claim 1, wherein immunizing antigen is at least one of a monomer, dimer, and trimer.

6. The method for detecting the presence of pork in a heat-processed food according to claim 1, wherein the proteins other than porcine proteins are proteins selected from the group consisting of proteins of cow, sheep, chicken, and mixtures thereof.

7. The method for detecting the presence of pork in a heat-processed food according to claim 1, wherein the detecting comprises:
placing a predetermined amount of a sample of the heat-processed food on a sample pad;
moving the sample to a labeled material-holding portion, a labeling reagent held at the labeled material-holding portion being dissolved in moisture of the sample;
passing the labeling reagent dissolved in the sample through a detection portion of a chromatography medium,
wherein, when the sample contains pork, an antigen in the pork reacts with the one or more polyclonal antibodies immobilized on the detection portion and the labeling reagent to form a complex by an antigen-antibody binding reaction, resulting in coloring in the detection portion, and
wherein, when the sample does not contain pork, the labeling reagent dissolved in the sample does not produce a binding reaction, resulting in no coloring in the detection portion; and
moving the sample to an absorbing portion, thereby removing the moisture from the sample.

8. The method for detecting the presence of pork in a heat-processed food according to claim 1, wherein the method detects pork contained in beef at a concentration of 0.1% by weight or more without a non-specific reaction.

9. The method for detecting the presence of pork in a heat-processed food according to claim 1, wherein the method detects pork contained in chicken at a concentration of 0.25% by weight or more without a non-specific reaction.

* * * * *